United States Patent
Brookins et al.

(10) Patent No.: US 6,875,092 B2
(45) Date of Patent: Apr. 5, 2005

(54) METHOD FOR THE MANUFACTURE OF A FEMORAL PROSTHESIS

(75) Inventors: Tracy A. Brookins, Warsaw, IN (US); Wesley C. Walker, Ft. Wayne, IN (US); Ted B Heindselman, Columbia City, IN (US); Robert J Mann, Plymouth, IN (US); Daniel O'Neil, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/394,628

(22) Filed: Mar. 21, 2003

(65) Prior Publication Data

US 2003/0186628 A1 Oct. 2, 2003

Related U.S. Application Data

(60) Provisional application No. 60/368,828, filed on Mar. 29, 2002.

(51) Int. Cl.$^7$ ................................................ B24B 1/00
(52) U.S. Cl. ............................ 451/57; 451/21; 623/22; 29/558
(58) Field of Search ....................... 451/57, 21; 623/22, 623/18, 19, 20; 29/558, 527.6

(56) References Cited

U.S. PATENT DOCUMENTS 4,753,044 A * 6/1988 Bula ........................... 451/65
5,560,096 A * 10/1996 Stephens ..................... 29/558
5,871,547 A * 2/1999 Abouaf et al. ............. 623/22.15

FOREIGN PATENT DOCUMENTS

| DK | DE003843046 A1 | * | 7/1989 |
| EP | 0 019 044 | | 3/1980 |
| EP | 0 398 064 B1 | | 4/1990 |

* cited by examiner

Primary Examiner—Joseph J. Hail, III
Assistant Examiner—Alvin J Grant
(74) Attorney, Agent, or Firm—Maginot, Moore & Beck (57) ABSTRACT

In accordance with certain aspects of the invention, an exemplary claim can define the steps of providing a rotating mount for the initially cast prosthesis in association with a numerically or computer controlled grinding machine. The grinding wheel is rotatably supported so that the wheel can translate vertically and axially relative to the axis of the workpiece, and can pivot in a plane generally parallel to the axis of the workpiece. In one step, the stem of the workpiece is rotated as the grinding wheel is held in position substantially perpendicular to the axis of the stem. The grinding wheel is then retracted and repositioned along the length of the stem through a series of successive positions. At each position, the grinding wheel is rotated in contact with the rotating workpiece. Once the grinding wheel is positioned at the transition region, the workpiece is preferably rotated through 180° on both sides of the transition region. When the grinding wheel is repositioned, it is not only moved axially relative to the workpiece, but also pivoted through a succession of angular positions until the grinding wheel is aligned with the shoulder of the prosthesis at the last position of the grinding wheel.

20 Claims, 5 Drawing Sheets

METHOD FOR THE MANUFACTURE OF A FEMORAL PROSTHESIS

REFERENCE TO RELATED APPLICATION

This application claims the benefit of the filing date of prior-filed commonly-owned provisional application, Ser. No. 60/368,828, filed on Mar. 29, 2002, in the name of the same inventors, which application is incorporated herein by reference.

BACKGROUND OF THE INVENTION

The present invention relates to the manufacture of joint prosthesis, and particularly a femoral prosthesis for a hip joint.

The femoral prosthesis for a prosthetic hip joint includes an elongated stem that is embedded within the medullary canal of the femur. The elongated stem body transitions at a transition region that terminates along the stem axis in a driver platform that provides a surface for driving the stem into the medullary canal. The transition region merges into a shoulder (which forms part of the driver platform) that is at an angle relative to the centerline of the stem that bears against a prepared surface of the femur. A neck and collar project from the shoulder, each configured to engage a ball joint component that forms part of the prosthetic hip joint.

The shoulder of the collar along with the angled transition region from the elongated stem to the platform present difficult manufacturing issues. While the stem is easily susceptible to formation through traditional milling operations, the angled shoulder and transition do not. The manufacturing issues can be complicated by a porous coating that is typically applied to the bone contacting surfaces of the femoral prosthesis.

At present, the femoral prosthesis is rough formed in a casting process. The entire prosthesis body can be surface ground using a known rotary grinding machine. The stem, neck and collar can be blended and polished using known techniques. However, the transition region and the shoulder must be hand blended and polished due to the complicated three-dimensional geometry.

However, the hand polishing process is fraught with inconsistencies. The typical hand polished prosthesis includes peaks and valleys in the surface, and poor blending throughout the transition region and under the shoulder. These inconsistencies can reduce the effectiveness of the fixation of the prosthesis to the femur. There is therefore a need for a manufacturing process that can eliminate these inconsistencies and that can produce a prosthesis that is held to a high tolerance.

SUMMARY OF THE INVENTION

In order to address this need, the present invention contemplates a method for the manufacture of a prosthesis, such as a femoral prosthesis, that exhibits a complicated outer geometry. In one embodiment of the invention, a method is provided that includes the initial step of providing a rotating mount for an initially cast prosthesis in association with a numerically or computer controlled grinding machine. The grinding wheel is rotatably supported so that the wheel can translate vertically and axially relative to the axis of the workpiece, and can pivot in a plane generally parallel to the axis of the workpiece.

In one step of the inventive method, the stem of the workpiece is rotated as the grinding wheel is held in position substantially perpendicular to the axis of the stem. The grinding wheel is then retracted and repositioned along the length of the stem through a series of successive positions. At each position, the grinding wheel is rotated in contact with the rotating workpiece. Once the grinding wheel is positioned at the transition region, the workpiece is preferably rotated through 180° on both sides of the transition region. When the grinding wheel is repositioned, it is not only moved axially relative to the workpiece, but also pivoted through a succession of angular positions until the grinding wheel is aligned with the shoulder of the prosthesis at the last position of the grinding wheel.

The present invention thus contemplates a method for manufacturing a femoral prosthesis comprising the steps of:

(a) generating a three-dimensional model of the intended final configuration of the femoral prosthesis having an elongated cylindrical stem, a proximal portion defining a shoulder adjacent the transition portion, and a transition portion between the stem and the proximal portion having opposite substantially flat sides and opposite intermediate edges, and;

(b) producing a rough prosthesis workpiece having the approximate size and shape of the intended final configuration;

(c) mounting the workpiece in a workpiece support operable to rotate the workpiece;

(d) contacting a rotating grinding wheel with the stem of the workpiece while the workpiece is rotated through 360°;

(e) retracting the grinding wheel from the workpiece and repositioning the grinding wheel along the length of the stem;

(f) repeating steps (d) and (e) from an initial position at one end of the stem to a final position at the opposite end of the stem;

(g) contacting the rotating grinding wheel with one intermediate edge of the transition portion of the workpiece adjacent the stem;

(h) rotating the workpiece through 180° while the grinding wheel is in contact with one of the flat sides of the workpiece until the grinding wheel reaches the opposite intermediate edge of the transition portion;

(i) retracting the grinding wheel from the workpiece;

(j) repositioning the grinding wheel relative to the workpiece by pivoting the grinding wheel about a vertical axis and translating the workpiece toward the proximal portion of the workpiece; and (k) repeating steps (g) through (j) until the grinding wheel is positioned at the proximal portion of the workpiece;

(l) rotating the workpiece 180°;

(m) contacting the rotating grinding wheel with the opposite intermediate edge of the transition portion of the workpiece adjacent the stem;

(n) rotating the workpiece through 180° while the grinding wheel is in contact with the opposite flat side of the workpiece until the grinding wheel reaches the opposite intermediate edge of the transition portion;

(o) retracting the grinding wheel from the workpiece;

(p) repositioning the grinding wheel relative to the workpiece by pivoting the grinding wheel about a vertical axis and translating the workpiece toward the proximal portion of the workpiece;

(q) repeating steps (m) through (p) until the grinding wheel is positioned at the proximal portion of the workpiece.

Certain steps of the inventive method are repeated for different types of grinding surfaces. For instances, in an initial grinding process, the grinding wheel includes a rough grinding surface. In subsequent grinding operations, the grinding wheel is a grit polishing wheel and a buffing wheel.

It is one object of the present invention to provide a method for the manufacture of a femoral prosthesis that is capable of implementation using a numerically controlled grinding machine. One benefit of the invention is that certain previously required manual steps in the manufacture of the prosthesis are eliminated, while certain previously required mechanical machining steps are improved in efficiency and production rate.

Other objects and benefits of the present invention will become apparent from the following written description considered in conjunction with the accompanying figures.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
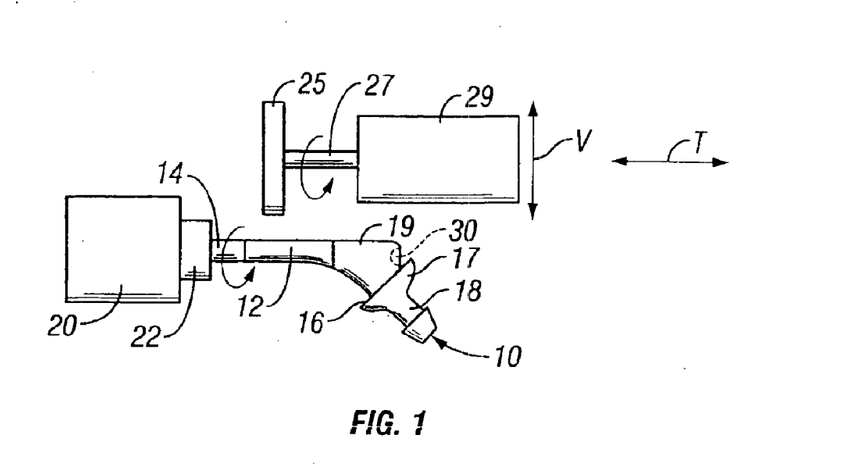
FIG. 1 is a side view of a femoral prosthesis mounted within a numerically controlled grinding machine.
Figure 2:
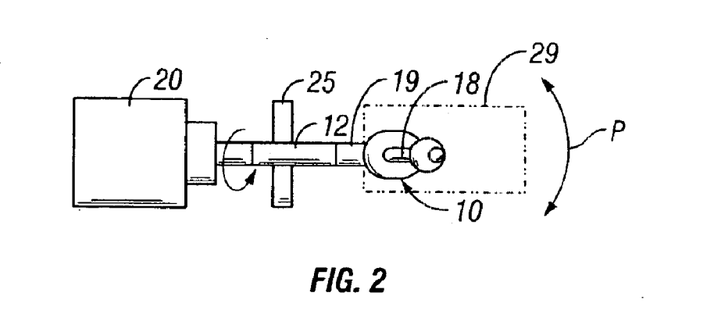
FIG. 2 is a top view of the prosthesis mounted within the grinding machine shown in FIG. 1.
Figure 4:
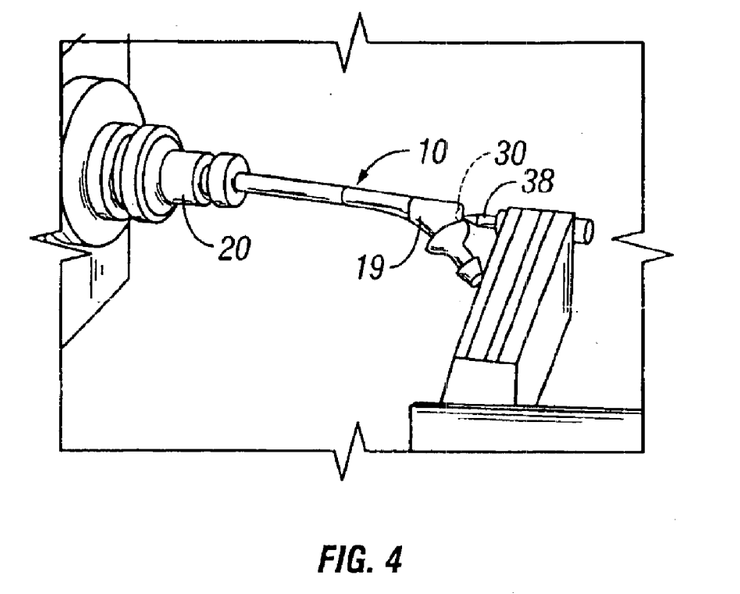
FIG. 4 is a top view of the prosthesis mounted within the grinding machine in a first step of the invention.

The present invention contemplates a process for using a numerically controlled machine, such as a rotary grinding machine, for performing the intricate steps for three-dimensional machining of the transition region and shoulder of a femoral prosthesis. Referring to FIGS. 1, 2 and 4, it can be seen that a rough cast femoral prosthesis 10 is mounted within a chuck 22 of a secondary spindle 20 of a grinding machine. The prosthesis includes an elongated stem 12 that terminates in a sacrificial end 14 that is engaged within the chuck 22. The spindle 20 rotates the prosthesis 10 about the axis of the stem 12.

The femoral prosthesis further includes a transition region 19 between the stem 12 and the proximal portion of the prosthesis. The transition region defines a locator feature 30 that can provide a seat for a centering tool, as described herein. This proximal portion includes a shoulder 16 of a collar or drive platform 17. A neck 18 projects from the collar 17 at a known angle. While the stem 12 is cylindrical, the transition region 19 is generally flat on its opposite faces with rounded side edges. The transition region 19 orients the shoulder 16 at an angle to the axis of the stem. Until now this angle has been an impediment to any type of standard machining, such as numerically controlled, other than a hand machining operation.

The workpiece support spindle 20 is part of a grinding machine that includes a grinding wheel 25. The grinding wheel 25 is mounted on a rotating axle 27 that is driven by a numerically controlled motor 29. The motor 29 is supported so that it can translate vertically, as indicated by the arrows V in FIG. 1, and axially as indicated by the arrows T. The motor 29 can also be controlled to pivot in the plane generally parallel to the axis of the supported workpiece, in this case the axis of the stem 12. This pivoting movement is indicated by the arrows P in FIG. 2. The grinding wheel includes a grinding surface 35 (see FIG. 6) that is different for different grinding steps of the present inventive process, as described in more detail herein.

Figure 6:
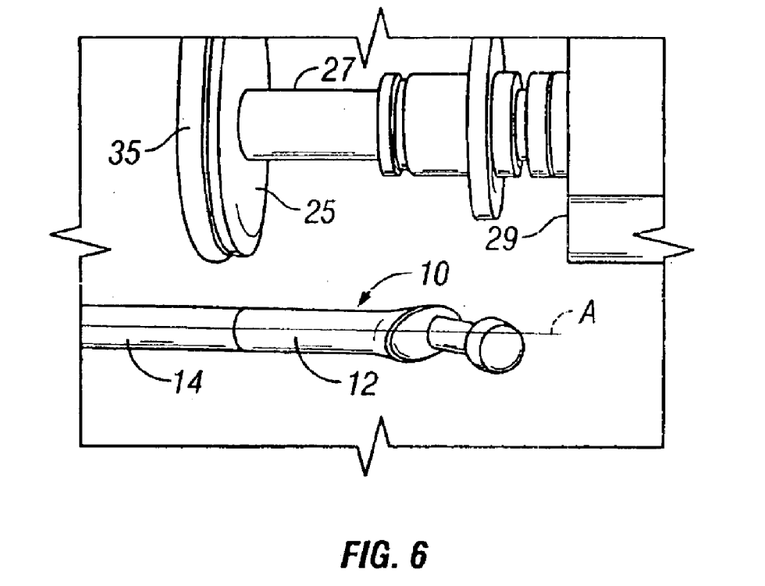
FIG. 6 is a side view of the prosthesis mounted within the grinding machine, as depicted in FIG. 4, with the grinding wheel shown positioned at the beginning of its grinding path.
Figure 7:
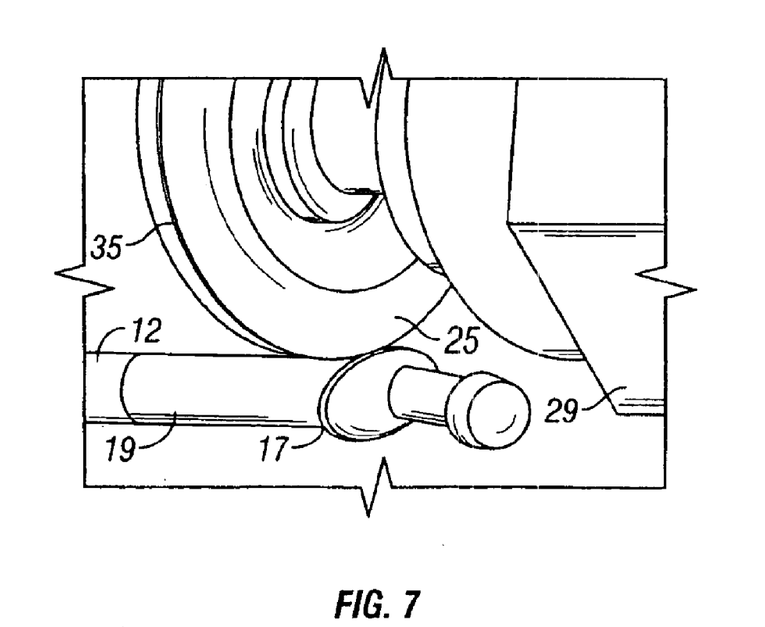
FIG. 7 is a side view of the prosthesis mounted within the grinding machine, as depicted in FIG. 4, with grinding wheel shown positioned adjacent the driver platform of the prosthesis.

The three movements—i.e. vertical V, pivoting P and translation T—are controlled by the numerical control system. In addition, the motor 29 can be mounted so that it can freely translate in the vertical direction V in response to the contour of the workpiece. For instance, as the effective diameter of the rotating workpiece increases, the motor can be free to translate upward to maintain an even machining pressure on the workpiece. With these degrees of freedom of movement, the grinding machine can transition the grinding wheel 25 from its initial position shown in FIG. 5, to its starting position for the grinding operation shown in FIG. 6, to its ending position directly adjacent the shoulder 16 as shown in FIG. 7.

Figure 3:
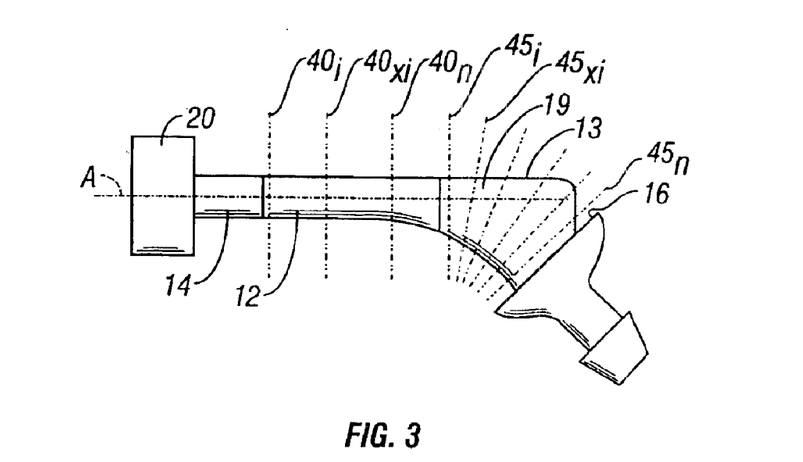
FIG. 3 is an enlarged view of a femoral prosthesis with varying positions of the grinding wheel depicted.

These vertical V and pivoting P movements of the grinding wheel are utilized to permit numerically controlled machining of the femoral prosthesis 10, in accordance with one aspect of the present invention. In one embodiment of the invention, the grinding wheel 25 can be positioned at the end of the prepared stem 12 adjacent the sacrificed end 14, as shown in FIG. 6. The grinding wheel is rotated about its axle 27, which is substantially parallel to the axis A of the stem 12, so that the wheel contacts the stem perpendicular to the axis A. The grinding wheel is initially situated at a position 40$i$ relative to the unfinished stem 12, as depicted in FIG. 3.

The rotating spindle 20 can rotate the prosthesis 10 as the grinding wheel is operating to perform a grinding or polishing operation at the position 40$i$. A centering fixture 38 engages the locator feature 30 formed in the end of the transition region 19, as shown in FIG. 4. The centering fixture engages the prosthesis 10 along the longitudinal axis of the workpiece so that the prosthesis is fully supported during its rotation.

Once the grinding or polishing operation is finished at the position 40i, the numerical control then retracts the grinding wheel from the workpiece and repositions the wheel upstream along the length of the stem 12. The wheel is then moved into engagement with the stem at the new position. The prosthesis 10 is rotated about its axis A by spindle 20 while the grinding wheel is rotated about the axis of its axle 27.

This numerically controlled movement of the grinding wheel continues to successive positions along the stem, such as an intermediate position 40xi and a final position 40n. The number of successive retractions, repositions, and engagements of the grinding wheel 27 to the stem 12 depends upon the width of the grinding wheel in relation to the length of the stem 12 from the sacrificed end 14 to the transition region 19. Throughout this length of the stem, the machining operation is facilitated by the 360° rotation of the workpiece about the axis of the stem. In a typical embodiment, the grinding wheel can have a width of 0.50" for a stem having a length of about 5" or more. Of course, a wider wheel can reduce the number of grinding steps, but may sacrifice surface quality. Throughout this length of the stem, the machining operation is facilitated by the 360° rotation of the workpiece about the axis of the stem.

The machining of the transition region 19 and shoulder 16 is complicated by the geometry of the prosthesis at this portion. In order to permit numerically controlled machining of the transition region 19, the present invention contemplates controlled pivoting of the grinding wheel motor 29, and therefore the grinding wheel 25 as the wheel traverses the length of the region 19. Thus, at position 45i the grinding wheel 25 can be oriented with its axis of rotation (or the axle 27) substantially parallel to the axis A of the stem 12. Preferably, the grinding wheel 25 engages the stem 12 at the back face 13 of the stem, or more specifically the workpiece is oriented relative to the grinding wheel as shown in FIG. 1. The spindle 20 is then controlled to rotate the prosthesis 10 through one-half rotation or 180° when machining the transition region 19.

In one aspect of the invention, the grinding wheel is retracted and the workpiece is rotated back to its initial position as shown in FIG. 1. The grinding wheel can then be re-engaged to the workpiece at the same location 45i and the spindle 20 can rotate the prosthesis 10 through a half rotation in the opposite direction to the first machining step.

In another feature of the inventive method, at the end of each grinding stroke, the workpiece 10 is rotated back to its initial position shown in FIG. 1. The motor 29 is controlled to retract the wheel and reposition the wheel at the next successive location, such as location 45xi. In repositioning the grinding wheel 25, the numerical control translates the wheel along the length of the stem, while also pivoting the wheel in the pivot direction P (FIG. 2). The wheel is thus pivoted to a predetermined angular orientation relative to the axis A of the stem. This repositioning process continues through several intermediate positions, such as position 45xi, and ending with the final position 45n immediately adjacent the shoulder 16.

The angular sweep of the grinding wheel 25 in each successive machining position 45i, 45xi, 45n, is based on the angle of the shoulder 16 relative to the axis A. The incremental angular repositioning of the grinding wheel is based on the width of the grinding wheel relative to the shoulder angle. It is contemplated that the grinding wheel will be repositioned many times in the transition region 19 in order to ensure a smooth, highly toleranced part. The number of times the wheel is repositioned can be determined in relation to a desired maximum scallop height, as measured from the lowest valley to the tallest peak on a pass of the grinding wheel across the workpiece.

In other words, it is known that any grinding operation produces peaks at the edges of the grinding wheel, and that these peaks prevail even with overlapped grinding paths. The peaks, and the difference between the peaks and valleys, can be minimized by increasing the number of overlapping grinding steps. The trade-off, of course, is that the grinding operation takes longer to complete because the increments between successive repositioning of the wheel are smaller. For an initial grinding operation, the acceptable maximum scallop height can be determined by the number of passes and/or the configuration of any subsequent polishing or blending wheel passing across the initial ground surface.

In accordance with the present invention, a series of grinding and polishing steps are conducted. For instance, in a first pass over the prosthesis after it is initially clamped within the grinding machine, the prosthesis is roughly ground to shape with a series of peaks and valleys. In a second pass, a grit polishing wheel can be used to remove the scallop height and blend the surface of the prosthesis. In a final pass, a buffing wheel can be used to create a highly polished mirror finish. Each of these passes can proceed according to the same numerical control or computer program—i.e., the grinding wheel follows the same path and number of incremental grinding steps regardless of the form of the wheel.

The invention further contemplates that a three-dimensional model of the finished product prosthesis can be provided to the numerical control or computer control system for the grinding machine. This full-scale three-dimensional model can be used by the control system to determine the appropriate movements of the grinding wheel as it is repositioned along the length of the prosthesis. Thus, a CNC tool path is developed using a three-dimensional full-scale computer model of the final product. The step-over amount for the grinding wheel can be calculated based on the acceptable scallop height.

Figure 5:
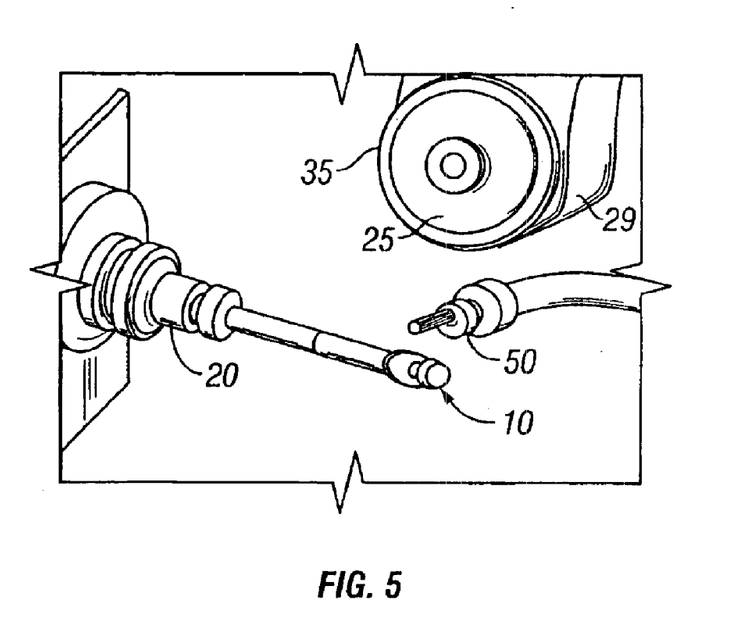
FIG. 5 is a perspective view of the prosthesis mounted within the grinding machine, as depicted in FIG. 4, with the grinding wheel shown in its initial position.

The orientation of the actual workpiece during the grinding process can be verified by a numerically controlled probe, such as the probe 50 shown in FIG. 5, which then feeds the position information to the control software to adjust the control commands appropriately. The probe 50 is used to determine the initial position of the workpiece before the numerically controlled machining operation is commenced. This initial position determination is processed by the CNC control algorithms in a known manner to adjust or offset the incremental positions of the grinding wheel in accordance with the CNC tool-path model.

Figure 8:
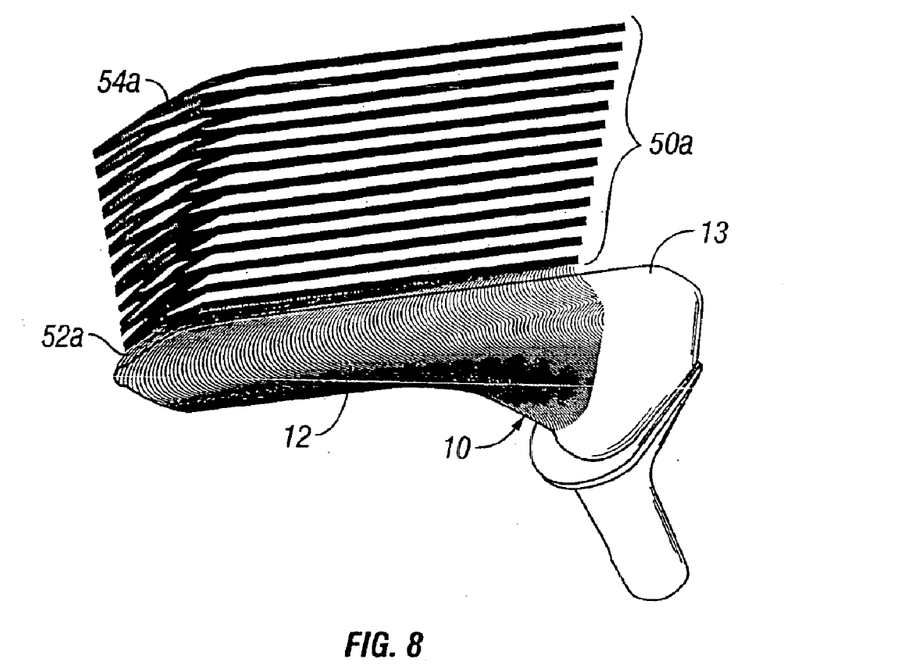
FIG. 8 is a graphic representation of a grinding wheel tool path across the elongated stem of a femoral prosthesis in accordance with one aspect of the machining method of the present invention.
Figure 9:
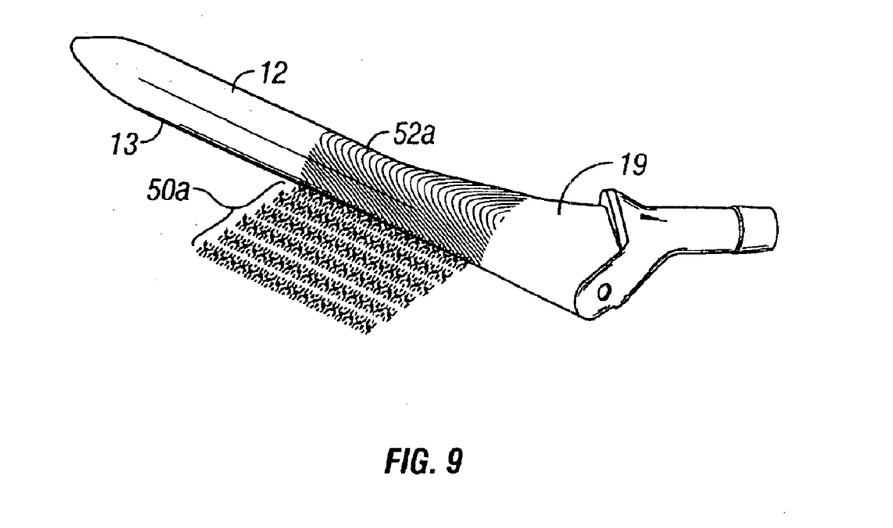
FIG. 9 is a graphic representation of a portion of the grinding wheel tool path depicted in FIG. 8 viewed from a different viewing angle.

Referring to FIGS. 8–11, graphic representations of the tool movements in accordance with the present invention are depicted. The machining steps for the stem 12 are shown in FIGS. 8 and 9. The lines 50a show the grinding wheel retraction and engagement/approach movement—i.e., the movement of the grinding wheel toward and away from the prosthesis as the grinding wheel is indexed along the positions 40i–40n. The lines 52a show the point of contact between the grinding wheel and the workpiece during the grinding operation. While the grinding wheel does not translate or rotate during a grinding step, the workpiece/ prosthesis itself does rotate 360° about its axis. The grinding step starts and finishes at the back face 13 of the prosthesis 12.

As can be appreciated from FIG. 9, the stem grind extends into a portion of the transition region 19. Since the grinding wheel is mounted to permit free vertical movement, the wheel will translate upward as the wheel rides along the increased dimension of the transition region.

The lines 54a at the distal end of the prosthesis show the path of the grinding wheel as it is repositioned relative to the workpiece. In particular, the grinding wheel is rotated relative to the axis of the workpiece to produce the tapered distal tip shown in the figure. This step can be a supplemental step to the basic grinding process, given that the distal end of the stem constitutes the sacrificial portion 14.

Figure 10:
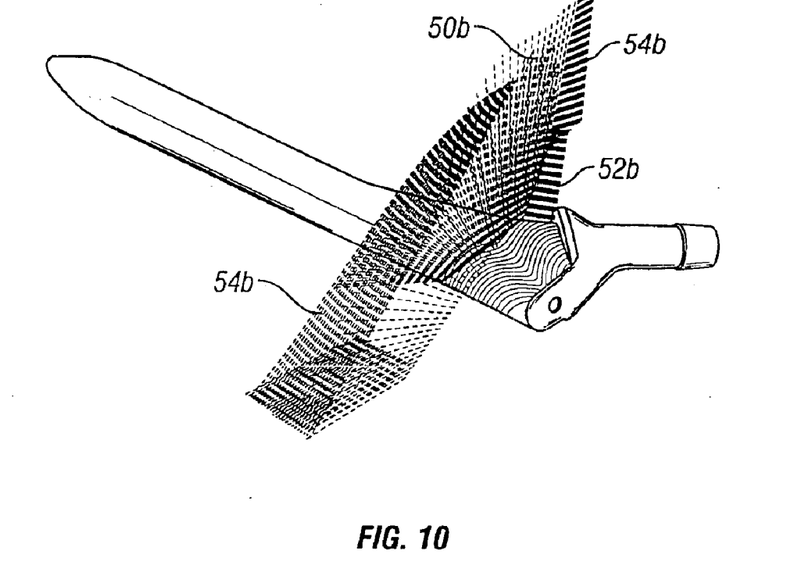
FIG. 10 is a graphic representation of a grinding wheel tool path across the transition zone of a femoral prosthesis in accordance with a further aspect of the machining method of the present invention.
Figure 11:
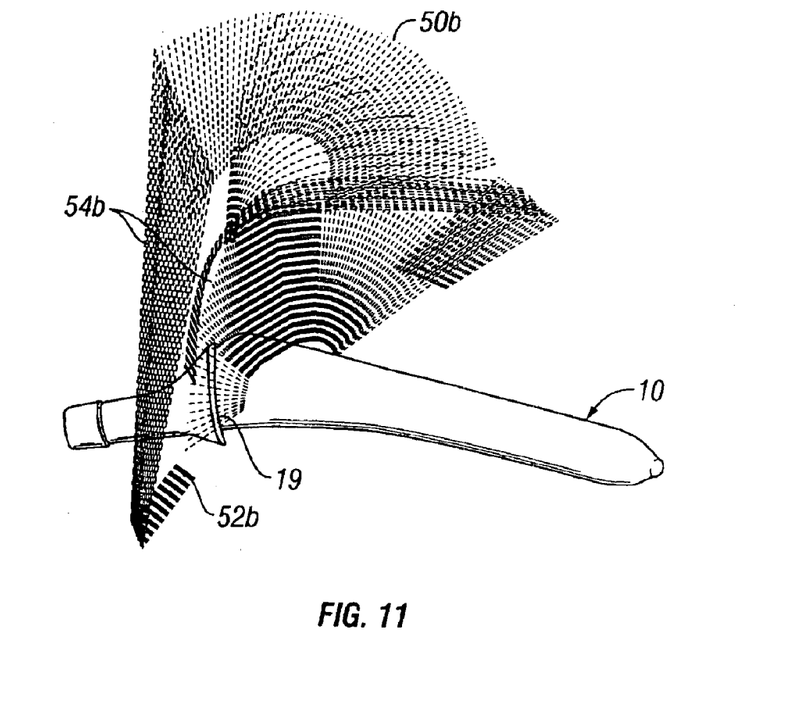
FIG. 11 is a graphic representation of the grinding wheel tool path depicted in FIG. 10 viewed from a different viewing angle.

In FIGS. 10 and 11, the machining steps for machining the transition region 19 are illustrated. The approach and retract movement of the grinding wheel into and out of engagement with the workpiece corresponds to lines 50b, while the grinding engagement with the workpiece follows lines 52b.

The repositioning movements for the grinding wheel are illustrated as lines 54b. In particular, it can be seen that the grinding wheel is not only pivoted (in the direction P as shown in FIG. 2), it is also translated along the length of the transition region. It should be understood that once the grinding wheel is positioned in one of its many incremental grinding positions shown in FIGS. 10, 11, the prosthesis workpiece 10 is rotated about the axis of the stem 12. Since the grinding wheel is mounted to permit vertical translation (in the direction V shown in FIG. 1), the wheel will move upward as the workpiece rotates and the wheel rides up the flat surface to the opposite edge. When the wheel reaches the opposite edge, the wheel is retracted, as indicated by the lines 50b in FIG. 11, and returned to its starting position at the opposite edge. The wheel is then indexed by pivoting and translating as indicated by the lines 54b to the next incremental position on the transition region 19.

This CNC controlled path continues on one flat side of the workpiece. The prosthesis workpiece is then rotated 180° to expose the opposite flat side of the transition region to the grinding wheel. The same process is repeated on the opposite side.

Once the initial grinding is completed, the originally rough workpiece is now smoother but with scallops along its length. These scallops are removed by a subsequent grinding sequence in which the original grinding wheel is replaced with a grit polishing wheel. A third sequence can follow in which the grit polishing wheel is replaced by a buffing wheel. With each sequence, the grinding wheel follows the same CNC controlled path along the stem 12 and transition region 19.

From one aspect, the present invention contemplates first creating a three-dimensional full scale model of the intended final design. A CAD based system can be used to produce this model. This 3D model can then be passed through a CAM system to generate a series of CNC tool-path instructions that will control the 3D movement of the grinding wheel. The CAM system can calculate the step-over amount for the grinding wheel as it is indexed along the length of the workpiece. This calculation is based on the width of the grinding wheel and the desired acceptable scallop height.

To commence the manufacturing process, the rough prosthesis workpiece is manufactured that has the approximate size and shape of a final prosthesis. This rough prosthesis can be formed by casting, forging or rough machining. The rough prosthesis is then loaded into the CNC grinder, with the sacrificial end 14 mounted within the workpiece support 20. The proximal end is preferably also supported by a center support so that the workpiece will spin stably about its axis.

With the workpiece so supported, the CNC grinder can be operated according to the CAM generated tool-path instructions. In grinding the stem, the workpiece can be continuously rotated as the grinding wheel is held at each successive position 40i along the length of the stem. On the other hand, when the transition portion 19 is being ground, the workpiece is only rotated through 180°, as explained above. It is understood that the grinding wheel is supported to permit free translation in the vertical direction relative to the workpiece (direction V in FIG. 1) so the wheel will move up and down with the changes in vertical projection of the workpiece as it rotates about its own axis. In the case of the stem, little vertical variation is expected, but in the case of the transition portion, the wheel will translate more because this portion is non-circular.

It is understood that the CNC tool-path instructions control when the grinding wheel is retracted from the workpiece, repositioned and extended back into contact with the workpiece. The repositioning can be simply translating the wheel by the step-over amount, as necessary for machining the circular stem. On the other hand, at the transition portion, the repositioning requires pivoting the wheel (direction P in FIG. 2) and translating toward the shoulder 16.

Once the initial grind is completed, secondary polishing is completed by engaging a grit polishing wheel with the prosthesis. This grit wheel removes the scallop height and blends the workpiece surface. The secondary polishing can follow the same CNC tool-path instructions as for the initial grind, since any change in vertical projection of the workpiece by the initial grinding step will be accommodated by the vertical freedom of movement of the grinding wheel. The final polishing step also follows the same CNC tool-path, but uses a buffing wheel.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for manufacturing a femoral prosthesis comprising the steps of:

(a) generating a three-dimensional model of the intended final configuration of the femoral prosthesis having an elongated cylindrical stem, a proximal portion and a transition portion between the stem and the proximal portion, said proximal portion defining a shoulder adjacent the transition portion, and said transition portion having opposite substantially flat sides and opposite intermediate edges, and;

(b) producing a rough prosthesis workpiece having the approximate size and shape of the intended final configuration;

(c) mounting the workpiece in a workpiece support operable to rotate the workpiece;

(d) contacting a rotating grinding wheel with the stem of the workpiece while the workpiece is rotated through 360°;

(e) retracting the grinding wheel from the workpiece and repositioning the grinding wheel along the length of the stem;

(f) repeating steps (d) and (e) from an initial position at one end of the stem to a final position at the opposite end of the stem;

(g) contacting the rotating grinding wheel with one intermediate edge of the transition portion of the workpiece adjacent the stem;

(h) rotating the workpiece through 180° while the grinding wheel is in contact with one of the flat sides of the workpiece until the grinding wheel reaches the opposite intermediate edge of the transition portion;

(i) retracting the grinding wheel from the workpiece;

(j) repositioning the grinding wheel relative to the workpiece by pivoting the grinding wheel about a vertical axis and translating the workpiece toward the proximal portion of the workpiece; and (k) repeating steps (g) through (j) until the grinding wheel is positioned at the proximal portion of the workpiece;

(l) rotating the workpiece 180°;

(m) contacting the rotating grinding wheel with the opposite intermediate edge of the transition portion of the workpiece adjacent the stem;

(n) rotating the workpiece through 180° while the grinding wheel is in contact with the opposite flat side of the workpiece until the grinding wheel reaches the opposite intermediate edge of the transition portion;

(o) retracting the grinding wheel from the workpiece;

(p) repositioning the grinding wheel relative to the workpiece by pivoting the grinding wheel about a vertical axis and translating the workpiece toward the proximal portion of the workpiece;

(q) repeating steps (m) through (p) until the grinding wheel is positioned at the proximal portion of the workpiece.

2. The method for manufacturing a femoral prosthesis according to claim 1, in which the grinding wheel includes a rough grinding surface.

3. The method for manufacturing a femoral prosthesis according to claim 1, in which the grinding wheel is a grit polishing wheel.

4. The method for manufacturing a femoral prosthesis according to claim 1, in which the grinding wheel is a buffing wheel.

5. The method for manufacturing a femoral prosthesis according to claim 1, in which the grinding wheel is initially a rough grinding surface, and then steps (d) through (q) are subsequently repeated where grinding wheel is a grit polishing wheel.

6. The method for manufacturing a femoral prosthesis according to claim 5, wherein steps (d) through (q) are subsequently repeated where the grinding wheel is a buffing wheel.

7. The method for manufacturing a femoral prosthesis according to claim 1, wherein steps (d) through (f) are performed before steps (g) through (q).

8. The method for manufacturing a femoral prosthesis according to claim 1, wherein steps (d) through (f) commence with the grinding wheel at the end of the stem adjacent the workpiece support.

9. A method for manufacturing a femoral component of a hip joint prosthesis, comprising the steps of:

producing a rough femoral component workpiece having (i) a stem portion defining a stem axis, (ii) a proximal portion having a shoulder, and (iii) a transition portion having a first end located adjacent to the stem portion and a second end located adjacent to the shoulder of the proximal portion, the transition portion extending at an oblique angle in relation to the stem axis;

shaping the stem portion by contacting the stem portion with a grinding wheel, the grinding wheel defining a grinding wheel axis, the stem axis and the grinding wheel axis being parallel in relation to each other during the stem portion shaping step; and moving the grinding wheel so that the stem axis and the grinding wheel axis become non-parallel in relation to each other; and shaping the transition portion by contacting the stem portion with the grinding wheel, the stem axis and the grinding wheel axis being non-parallel in relation to each other during the transition portion shaping step.

10. The method of claim 9, wherein the grinding wheel includes a rough grinding surface.

11. The method of claim 9, wherein the grinding wheel includes a grit polishing wheel.

12. The method of claim 9, wherein the grinding wheel includes a buffing wheel.

13. The method of claim 9, wherein the stem axis and the grinding wheel axis form an angle of at least 22.5° during the transition portion shaping step.

14. A method for manufacturing a femoral component of a hip joint prosthesis, comprising the steps of:

(a) producing a rough femoral component workpiece having (i) a stem portion defining a stem axis, (ii) a proximal portion having a shoulder, and (iii) a transition portion having a first end located adjacent to the stem portion and a second end located adjacent to the shoulder of the proximal portion, the transition portion extending at an oblique angle in relation to the stem axis;

(b) first shaping the stem portion by contacting the stem portion with a grinding wheel, the grinding wheel defining a grinding wheel axis, the stem axis and the grinding wheel axis being parallel in relation to each other during the first stem portion shaping step;

(c) after step (b), retracting the grinding wheel from contact with the workpiece and repositioning the grinding wheel along the length of the stem portion;

(d) after step (c), second shaping the stem portion by contacting the stem portion with the grinding wheel, the stem axis and the grinding wheel axis being parallel in relation to each other during the second stem portion shaping step;

(e) after step (d), pivoting the grinding wheel so that the stem axis and the grinding wheel axis are non-parallel in relation to each other;

(f) after step (e), first shaping the transition portion by contacting the stem portion with the grinding wheel, the stem axis and the grinding wheel axis being non-parallel in relation to each other during the first transition portion shaping step;

(g) after step (f), repositioning the grinding wheel relative to the workpiece by further pivoting the grinding wheel in relation to the workpiece; and (h) after step (g), second shaping the transition portion by contacting the stem portion with the grinding wheel, the stem axis and the grinding wheel axis being non-parallel in relation to each other during the second transition portion shaping step.

15. The method of claim 14, wherein the grinding wheel includes a rough grinding surface.

16. The method of claim 14, wherein the grinding wheel includes a grit polishing wheel.

17. The method of claim 14, wherein the grinding wheel includes a buffing wheel.

18. The method of claim 14, wherein the grinding wheel includes a rough grinding surface during steps (b) through (h), and further comprising:
(i) after step (h), altering the grinding wheel so that the grinding wheel possesses a grit polishing wheel; and
(j) after step (i), repeating steps (b) through (h) while the grinding wheel possesses the grit polishing wheel.

19. The method of claim 18, further comprising:
(k) after step (j) altering the grinding wheel so that the grinding wheel possesses a buffing wheel; and
(l) after step (k), repeating steps (b) through (h) while the grinding wheel possesses the buffing wheel.

20. The method of claim 14, wherein the stem axis and the grinding wheel axis form an angle of at least 22.5° during the second transition portion shaping step.

* * * * *